(12) United States Patent
Schertiger

(10) Patent No.: US 9,693,889 B2
(45) Date of Patent: Jul. 4, 2017

(54) URINE COLLECTION DEVICE AND A METHOD OF EMPTYING URINE FROM A CONTAINER

(71) Applicant: Coloplast A/S, Humlebaek (DK)

(72) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 15/034,434

(22) PCT Filed: Oct. 31, 2014

(86) PCT No.: PCT/DK2014/050357
§ 371 (c)(1),
(2) Date: May 4, 2016

(87) PCT Pub. No.: WO2015/067270
PCT Pub. Date: May 14, 2015

(65) Prior Publication Data
US 2016/0302960 A1  Oct. 20, 2016

(30) Foreign Application Priority Data

Nov. 7, 2013  (DK) .................................. 2013 70651

(51) Int. Cl.
*A47K 11/00* (2006.01)
*A61F 5/451* (2006.01)
*A47K 11/12* (2006.01)

(52) U.S. Cl.
CPC .............. *A61F 5/451* (2013.01); *A47K 11/12* (2013.01)

(58) Field of Classification Search
CPC ........................................................ A61G 9/006
USPC ................................................ 4/144.1–144.3
See application file for complete search history.

(56) References Cited

U.S. PATENT DOCUMENTS

| 3,473,532 | A | 10/1969 | Eisenberg |
| 4,723,944 | A | 2/1988 | Jensen |
| 4,772,278 | A | 9/1988 | Baber |
| 4,828,554 | A | 5/1989 | Griffin |
| 5,059,190 | A | 10/1991 | Novak |
| 5,745,926 | A | 5/1998 | Cailleteau |
| 6,129,714 | A | 10/2000 | Kocsi |
| 6,849,070 | B1 | 2/2005 | Hansen et al. |
| 7,846,142 | B2 | 12/2010 | Burgess et al. |
| 2009/0077734 | A1 | 3/2009 | Ledo |
| 2012/0116335 | A1 | 5/2012 | Tanghoej |

FOREIGN PATENT DOCUMENTS

| CN | 1984625 A | 6/2007 |
| CN | 201082210 Y | 7/2008 |
| DE | 2249132 A1 | 4/1973 |
| DE | 2442628 A1 | 3/1975 |
| DE | 2634567 A1 | 2/1978 |
| DE | 2936622 A1 | 3/1981 |

(Continued)

*Primary Examiner* — Lori Baker
(74) *Attorney, Agent, or Firm* — Coloplast Corp., Coloplast A/S; Nick Baumann

(57) ABSTRACT

A urine collection bag (1) comprising an anti-reflux valve in the form of a foil valve (8), located at the inlet (5) of the bag. The valve secures a liquid tight seal of the bag when filled and that no reflux occurs during catheterization. The bag comprises a tube member (11) that can be brought in a position so as to bypass the foil valve and the bag can be emptied in an easy and non-messy way.

12 Claims, 2 Drawing Sheets

(56) References Cited

FOREIGN PATENT DOCUMENTS

| | | | |
|---|---|---|---|
| DK | 147294 | A | 12/1994 |
| EP | 0106587 | A2 | 4/1984 |
| EP | 0748620 | A1 | 12/1996 |
| EP | 1357868 | A2 | 8/2002 |
| EP | 2133047 | B1 | 2/2011 |
| FR | 2326208 | A1 | 4/1977 |
| GB | 2134789 | A1 | 8/1984 |
| GB | 2239804 | A1 | 7/1991 |
| GB | 2441114 | A1 | 2/2008 |
| WO | 9923978 | A1 | 5/1999 |
| WO | 2006089600 | A1 | 8/2006 |
| WO | 2010130261 | A1 | 11/2010 |

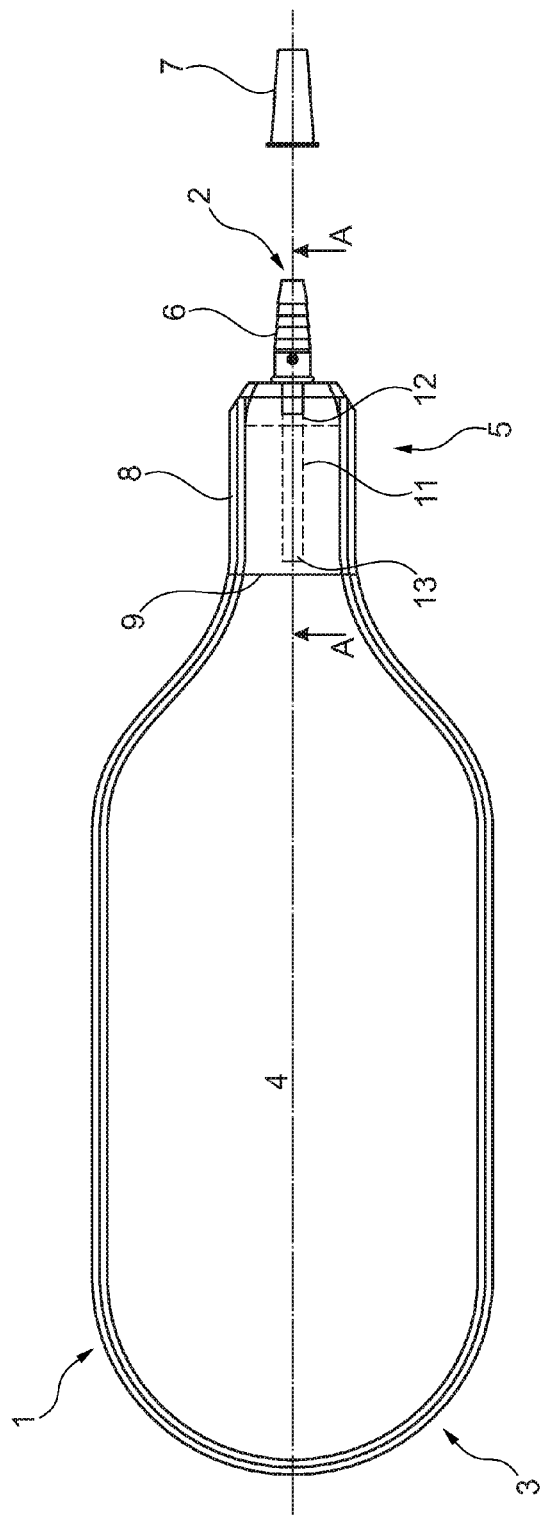
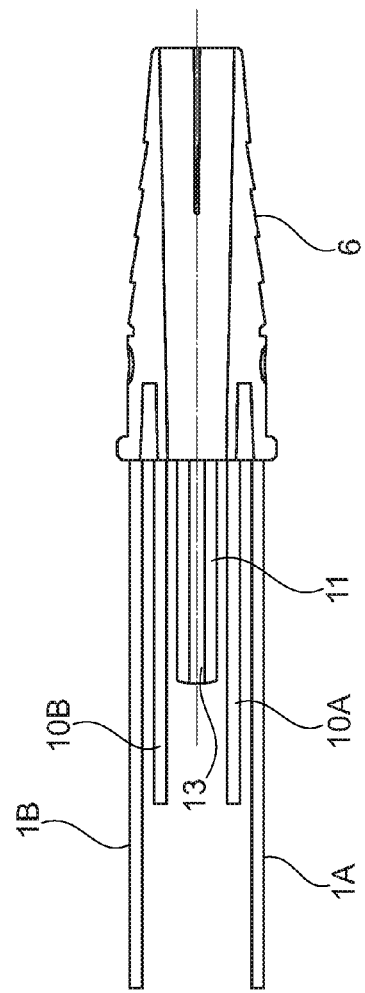
Fig. 1
Fig. 2

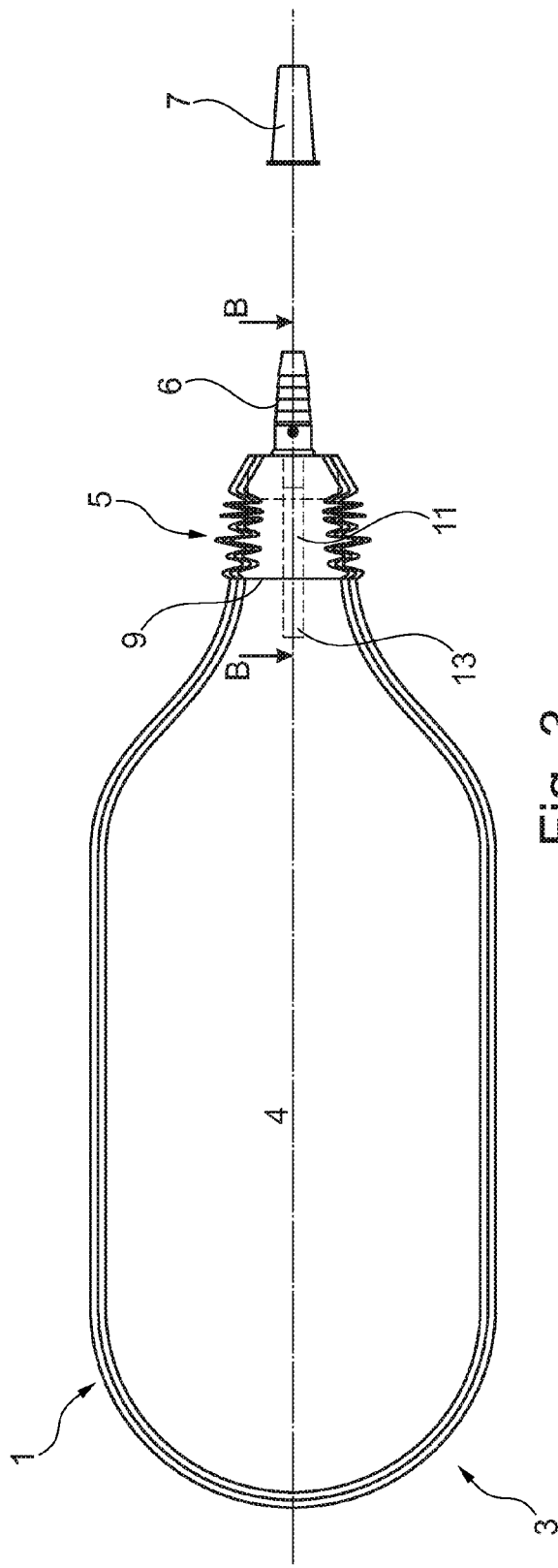
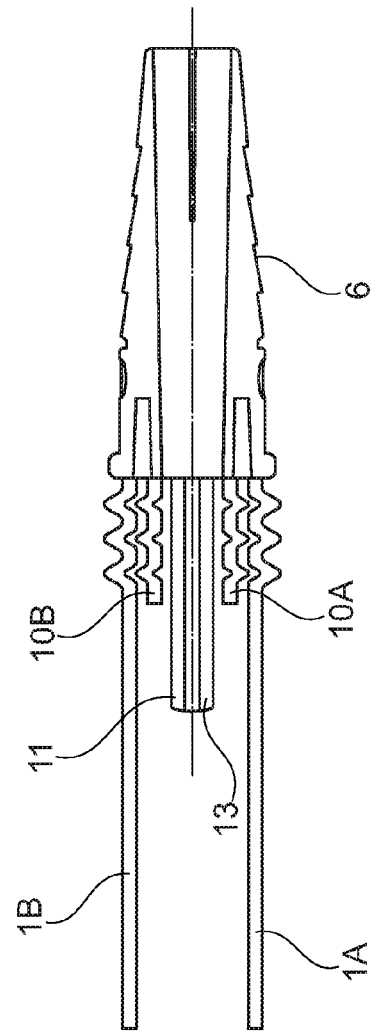
Fig. 3
Fig. 4

URINE COLLECTION DEVICE AND A METHOD OF EMPTYING URINE FROM A CONTAINER

FIELD OF THE INVENTION

The invention relates to a urine collection bag for use in connection with a catheter, the urine collection bag of which is provided with an anti-reflux valve at the inlet. The invention also relates to a method of emptying a urine collection bag.

BACKGROUND

For a large group of persons, intermittent catheterisation is a daily-life procedure that takes place several times a day. Typically, catheters for intermittent catheterisation are used by people suffering from urinary incontinence or by disabled individuals like para- or tetraplegics who may have no control permitting voluntary urination, and for whom catheterisation may be the way of urinating. Using an intermittent catheter, the bladder may be drained through a natural or artificial urinary canal.

The availability of catheter assemblies, which are compact and discrete to transport and dispose of, in addition to being easy to use, even for individuals with reduced dexterity, significantly improves quality of life for a large group of individuals. "Compact Female®" is a compact catheter, as described above, and is produced by Coloplast A/S.

In some situations, a user may wish to use a catheter with a urine bag connected to it, for example when a patient in a wheelchair is unable to move from the wheelchair to the toilet. Urine bags are typically made from sheets of a foil material joined along the edges.

The thickness of the urine bag is therefore very small, but due to the plane dimensions of the urine bag, it is rather indiscrete. The filled urine bag may be transported to the closest disposal bin or it may be emptied into the toilet. Draining the bag, however, may be difficult, due to the anti-reflux valve, so the bag has to be torn open and the urine poured out. This action may obviously easily become messy and the empty bag may be wet and unhygienic to hold in a handbag.

Thus, there is still a need for an easy and non-messy way of emptying of a urine bag and dispose of it.

DESCRIPTION OF RELATED ART

WO 2010/130261 discloses a urine collection bag with an anti-reflux foil valve at the inlet. When the bag is to be emptied, the bag is torn open at the side of the bag and the content is poured out.

Danish patent No. 147 294 discloses a urine collection bag. The bag is provided with a foil valve at a side edge. The bag can be emptied by inserting a catheter through the foil valve and squeeze the content out or use gravity.

SUMMARY OF THE INVENTION

It is an object of the invention to provide a urine collection bag with an anti-reflux valve which is tight, but yet easy to bypass when the bag is to be emptied.

It is yet an object of the invention to provide a urine collection bag and a method of emptying it in a clean way.

A further object of the invention is to provide a urine collection bag that can be emptied without use of separate additional gear, such as catheters or tubes.

BRIEF DESCRIPTION OF THE DRAWING

FIG. 1 illustrates an embodiment of the invention,
FIG. 2 illustrates a cross-section of the section A-A in FIG. 1,
FIG. 3 illustrates the same embodiment in emptying configuration and
FIG. 4 illustrates a cross-section of section B-B of FIG. 3.

DETAILED DESCRIPTION OF THE INVENTION

In a first aspect, the invention relates to a urine collection bag comprising an end with an opening at the top and a closed bottom at an opposite end defining a longitudinal direction of the bag between the opening and the bottom and a transverse direction of the bag transverse to the longitudinal direction, an inlet at the opening extending from the opening and a length into the bag, the inlet being an anti-reflux valve in form of a foil-valve with four layers of foil welded together in the longitudinal direction defining a width of the inlet between the welds in the transverse direction and the length of the inlet as a length of the foils in the longitudinal direction, wherein the inlet is further provided with a tube member having a first end being attached at the opening of the bag and a second end extending in the longitudinal direction of the bag, the tube member having a length being shorter than the length of the foil valve.

The length of the tube member may be less than 90%, such as less than 80%, 75%, 70%, 60%, or even less than 50% of the length of the foil valve. In one embodiment the length of the tube is 50-70% of the length of the foil valve.

The tube member may be a hollow, cylindrical member enabling fluid connection between the outside of the bag and the inside of the bag. The tube may have a diameter of less than 10 mm, such as between 2 and 8 mm, between 2 and 6 mm, or even between 3 and 5 mm. The tube may be unreleasably attached to the opening of the bag and/or to the connector.

The foil valve working as an anti-reflux valve enables liquid to enter the bag through the tube member and the foil valve, but does not allow liquid from the bag to escape through the foil valve. As long as the second end of the tube member is inside the foil valve, i.e. the tube member being shorter than the foil valve, the liquid in the bag cannot escape from the bag as the foil valve provides a liquid tight seal. When the bag is to be emptied, the inlet, including the foil valve is pushed back towards the opening of the bag, exposing the second end of the tube member into the liquid containing cavity of the bag and fluid can the pass through the tube member, from the bag to outside of the bag, by squeezing the bag.

When finished emptying of the bag, the inlet is straightened out again, bringing the second end of the tube member back into the starting position, where the foil valve is closed. The bag is emptied without the user getting into contact with the fluid content, for example by tearing an opening in the bag or by inserting a catheter—and ending up with a bag in one hand and a wet catheter in the other hand. Everything needed for emptying the bag is included in the bag, the user does not get messy fingers, and the bag stays clean on the outside.

The opening of the bag may be provided with a connector. The connector facilitates liquid tight connection to a catheter or an extension tube. The connector may be welded or otherwise attached to the opening. The first end of the tube member may be attached to the connector, for example by welding.

The bag may be provided with closing means, such as a cap. The closing means may be in the form of a reclosable cap fitted to the connector.

The second end of the tube member, being the end pointing towards the bag may be provided with a rounded tip portion such as a tip portion having a surface without sharp edges in order to minimize the risk of unintentional perforation of the bag.

The tube member may be flexible, semi-rigid or rigid. It should be rigid enough not to collapse during use. A soft and flexible tube member may facilitate packing of the bag into a very small volume.

The second end of the tube member may be provided with at least one opening at a side of the tube member, or the tube member may be provided with a hole at the end of the tube member, at the tip portion.

At least a part of the tube member may be colored. In order to clearly visualize the correct position of the tube member with regard to emptying of the bag, the tube member or part of it, such as the tip portion, may be provided with a color distinguishing it from the surroundings. If the bag is transparent it will be easy to see when the tube member is pushed through the valve and emptying of the bag may begin.

In a second aspect, the invention relates to a method of emptying an urine collection bag, comprising the steps of: providing a urine collection bag comprising an end with an opening at the top and a closed bottom at an opposite end defining a longitudinal direction of the bag between the opening and the bottom and a transverse direction of the bag transverse to the longitudinal direction, an inlet at the opening extending from the opening and a length into the bag, the inlet being an anti-reflux valve in form of a foil-valve with four layers of foil welded together in the longitudinal direction defining a width of the inlet between the welds in the transverse direction and the length of the inlet as a length of the foils in the longitudinal direction, the inlet is further provided with a tube member having a first end being in fluid connection with the opening of the bag and a second end extending in the longitudinal direction of the bag, the tube member having a length being shorter than the length of the foil valve, pushing the inlet portion including the foil valve together in longitudinal direction (into an accordion-like configuration), thereby exposing the second end of the tube member into the closed bottom of the bag and emptying the bag through the tube member by squeezing the bag.

When the bag is empty, the inlet may be straightening out in order to re-establish the sealing effect of the foil valve.

After emptying of the bag, the bag may be closed with a cap in order to avoid any residual fluid in the tube member or connector to escape from the bag.

The bag may be folded or rolled in order to minimize its volume, thereby being discreet and easy to dispose of or bring in for example a handbag until it can be disposed of in a bin. The bag can be folded together to a minimum volume and is not space consuming.

A length-width relationship in a foil valve as described above is an advantage when it comes to stopping liquid from exiting the bag. The relatively long length of the valve enables the two additional foil layers to be closed together in a fluid tight closure.

In an embodiment, the width is between 1.5 cm and 2.5 cm. In a related embodiment, the length is between 4 cm and 8 cm.

When the user needs catheterization, he unfolds the bag, places it on a table or another suitable place, and prepares the catheter. Then he removes the cap from the bag, connects the connector to the catheter, and the catheter is then inserted into the urethra and the bladder is emptied by draining the urine into the bag. The urine is able to pass through the foil valve entering the bag, but is unable to leave the bag through the foil valve. Having finished catheterization, the user disconnects the bag from the catheter and optionally puts the cap back on. The cap is preferably liquid tight. The cap secures that any residual liquid in the tube does not leak from the connector to the surroundings. The user may then dispose of the filled bag, which may be difficult as it is indiscreet due to the size of the filled bag, or he may empty it. This is done by pushing the inlet together to expose the tube member, thereby bypassing the foil valve. The bag may then be emptied by turning it upside down; using gravity or light pressure, and the last drops may optionally be squeezed out of it by rolling or folding the bag. When emptied, the inlet is straightened and the cap may be put on again, and the bag is folded or rolled to minimize the volume and discarded. The empty bag will not leak and takes up minimum of volume in a handbag.

In this way the process of emptying the urine collection bag is controlled without splashing or getting the hands and surroundings contaminated with urine. A bag that has been torn open has a frayed edge being capable of collecting liquid droplets and may be difficult to clean. A bag being emptied by inserting a catheter may leave the user with a wet and dirty catheter to dispose of. The bag of the present invention facilitates easy, dry and clean emptying of the bag, with all there is needed is included in the bag, no need for extra catheters or extra packaging in order to keep the bag dry and clean on the outside during the emptying process.

The material for the bag is flexible and bendable so that it may be packed (for example by folding or rolling) in a configuration taking up as little space as possible. The bag may be folded at the end of the valve and then onto itself another three times. The bag may then be folded to a size corresponding to the length of the tube member. When this is done, the bag is easily folded in the other direction into a configuration small enough to fit in a small bag or a hand.

Because the bag is made of only a few pieces of foil, only a small amount of material is used. Besides the tube member, no further attachments need to be fitted into the bag. Furthermore, a foil bag consisting essentially of only welded foil layers is cheap and easy to produce.

DETAILED DESCRIPTION OF THE DRAWING

FIG. 1 and FIG. 2 illustrate a urine collection bag 1 according to the invention. This urine collection bag 1 is made of two foil layers 1A, 1B and is generally bottle-shaped with a top end with an opening 2 and a closed bottom end 3 with a wider collecting cavity 4. The two foil layers 1A and 1B are welded together along their outer contour so that it constitutes a closed bag. An inlet 5 of the bag 1 is placed at the top end, extending to the opening 2. A connector 6 is fluid tight attached to the inlet 5. The connector 6 may be suitable for connecting the bag to a catheter or an extension tube (not shown). The connector 6 may be fitted with a detachable cap 7 for liquid tight closure of the bag 1 and to avoid any liquid residues in the connector 6 or foil valve 8 to escape. This inlet 5 comprises an anti-reflux valve 8 made of four layers of foil, two of which are constituted by the foil layers 1A and 1B of the bag. In this embodiment, the anti-reflux valve 8 extends approximately ⅔ into the inlet 5 as indicated by the transverse line 9 showing the length of the extra foil layers, 10A and 10B of the foil valve 8. The anti-reflux valve 8 is made by welding the four layers 1A, 1B, 10A, 10B of foil together at the inlet 5 along the sides. In FIG. 2, showing a cross-section along A-A of the inlet 5 and the position of the foil layers 1A, 1B, 10A, 10B being exaggerated to elucidate how the layers work together. In the inlet 5, a tube member 11 is present; the tube member 11 being connected at the opening 2 to the connector 6 at a first end 12 and the second end 13 is extending in longitudinal direction towards the closed end 3, 4 of the bag 1, but does not extend further than the foil valve 8, 9.

FIG. 3 and FIG. 4 show the embodiment of FIGS. 1 and 2, where the inlet 5 comprising the foil valve 8 has been pushed towards the opening 2 and connector 6 to be compressed or crumpled into a folded, accordion-like configuration. This action exposes the second end 13 of the tube member 11, which now is in fluid connection with the collecting cavity 4 of the bag, bypassing the anti-reflux foil valve 8. Squeezing the sides of the bag 1, the bag can now be drained for liquid, the liquid being pushed through the tube member 11. When the bag is empty, the inlet 5 of the bag is straightened out again, hereby reintroducing the liquid seal of the foil valve 8 and making the bag liquid tight again. The bag can now be folded or rolled to minimize volume and transported for example in a handbag to the nearest disposal bin. The cap 7 may be put over the connector 6 in order to withhold any liquid droplets left in the connector 6 or foil valve 8.

The invention claimed is:

1. A urine collection device comprising:
   a first layer sealed to a second layer to define a bag having a first end that is sealed closed and a second end that is provided with an opening, and an inlet section communicating with the opening, where the inlet section extends an inlet length away from the second end of the bag;
   a valve formed in the inlet section to communicate with the opening, the valve including a first film parallel to the first layer and a second film parallel to the second layer, where the first film has opposed lateral edges that are sealed to opposed lateral edges of the second film, with the valve extending into the bag by a valve length measured from the second end of the bag;
   a connector connected to the second end of the bag, the connector communicating with the opening; and
   a tube connected to the connector, the tube extending into the bag and having a tube length that is less than the valve length.

2. The urine collection device of claim 1, wherein the valve length is less than the inlet length.

3. The urine collection device of claim 1, wherein the valve length is longer than the tube length and so configured to prevent liquid from exiting the bag through the tube.

4. The urine collection device of claim 1, wherein the valve length is longer than the tube length and so configured to prevent liquid from exiting the bag through the tube, and wherein the valve is compressible in a direction of the second end of the bag to have a compressed valve length that is less than the tube length and so configured to allow liquid to exit the bag through the tube.

5. The urine collection device of claim 1, wherein the connector includes a reclosable cap.

6. The urine collection device of claim 1, wherein the tube has a first end connected to the connector and a second end that extends into the bag, and the second end of the tube is rounded.

7. The urine collection device of claim 1, wherein the tube is provided with an opening formed in a side wall of the tube.

8. The urine collection device of claim 1, wherein the bag is transparent and the tube is colored to provide a visual indicator relative to the transparent bag.

9. A method of emptying urine from a container, the method comprising:
   providing the urine collection device of claim 1 for collecting urine from a user into the bag;
   compressing the inlet section is a direction from the first end of the bag toward the second end of the bag and reducing the valve length that the valve extends into the bag as measured from the second end of the bag thus forming a reduced valve length, and exposing an exposed portion of the tube beyond the reduced valve length; and
   squeezing the bag and forcing the urine out of the bag through the tube and through the connector.

10. The method of claim 9, further comprising:
    extending the inlet section back to the valve length and covering the exposed portion of the tube with the valve.

11. The method of claim 9, further comprising:
    placing a cap onto the connector thus closing the connector.

12. The method of claim 9, further comprising:
    emptying the urine out of the bag to provide an empty bag; and
    folding the empty bag.

* * * * *